(12) United States Patent
Harata et al.

(10) Patent No.: US 9,340,808 B2
(45) Date of Patent: May 17, 2016

(54) SULFUR AMINO ACID-CONTAINING COMPOSITION

(71) Applicant: NISSHIN PHARMA INC., Chiyoda-ku (JP)

(72) Inventors: Masataka Harata, Fujimino (JP); Yuto Inagawa, Fujimino (JP)

(73) Assignee: NISSHIN PHARMA INC., Chiyoda-ku (JP)

( * ) Notice: Subject to any disclaimer, the term of this patent is extended or adjusted under 35 U.S.C. 154(b) by 0 days.

(21) Appl. No.: 14/381,076

(22) PCT Filed: Mar. 13, 2013

(86) PCT No.: PCT/JP2013/056901
§ 371 (c)(1),
(2) Date: Aug. 26, 2014

(87) PCT Pub. No.: WO2013/137284
PCT Pub. Date: Sep. 19, 2013

(65) Prior Publication Data
US 2015/0004658 A1    Jan. 1, 2015

(30) Foreign Application Priority Data
Mar. 14, 2012  (JP) ................................. 2012-057078

(51) Int. Cl.
| *C12P 13/12* | (2006.01) |
| *C12P 13/04* | (2006.01) |
| *A23L 1/305* | (2006.01) |
| *C12P 11/00* | (2006.01) |
| *A61K 36/00* | (2006.01) |

(52) U.S. Cl.
CPC ............... *C12P 13/12* (2013.01); *A23L 1/3051* (2013.01); *C12P 11/00* (2013.01); *A61K 36/00* (2013.01)

(58) Field of Classification Search
None
See application file for complete search history.

(56) References Cited

U.S. PATENT DOCUMENTS

| 6,468,565 B1 * | 10/2002 | Anno et al. ..................... 426/49 |
| 2003/0105093 A1 | 6/2003 | Yanagita et al. |

FOREIGN PATENT DOCUMENTS

| CN | 100548970 C * | 10/2009 | ............ C07C 323/58 |
| EP | 1080724 A1 * | 7/2001 | ........... A61K 31/195 |
| EP | 1230925 | 8/2002 | |
| JP | 99/08548 A1 | 2/1999 | |
| JP | 2007-084500 A | 4/2007 | |
| JP | 2007-210918 A | 8/2007 | |
| JP | 4172488 B2 | 10/2008 | |
| JP | 2009-254344 A | 11/2009 | |
| RU | 2346685 | 10/2008 | |
| RU | 2394581 | 3/2009 | |
| WO | 99/061015 A1 | 12/1999 | |

OTHER PUBLICATIONS

International Search Report and English translation of the Written Opinion issued Apr. 16, 2013 in PCT/JP2013/056901 filed Mar. 13, 2013.
John R. Whitaker, "Development of Flavor, Odor, and Pungency in Onion and Garlic" Advances in Food Research, vol. 22, 1976, pp. 73-133.
Takahiko Anno, "Shokubutsutai kara no Kanjo Ganryup Amin-san Ko Gan'yu Extract no Seizo" Technical Report of Japan Food Industry Center, No. 26, 2000, pp. 27-39.
Office Action as received in the corresponding Russian Patent Application No. 2014137158 dated Nov. 16, 2015 w/English Translation.

* cited by examiner

*Primary Examiner* — Karen Cochrane Carlson
*Assistant Examiner* — Natalie Moss
(74) *Attorney, Agent, or Firm* — Oblon, McClelland, Maier & Neustadt, L.L.P.

(57) ABSTRACT

Provision of a composition stably comprising a high concentration of sulfur amino acid derived from a plant belonging to the genus *Allium*. A method for producing a sulfur amino acid-comprising composition comprising: heating a plant belonging to the genus *Allium*; treating the plant belonging to the genus *Allium* thus heated with a γ-glutamyl bond cleaving enzyme; and subjecting the resulting enzyme-treated product to ion exchange chromatography.

9 Claims, No Drawings

SULFUR AMINO ACID-CONTAINING COMPOSITION

This application is a National Stage of PCT/JP2013/056901 filed Mar. 13, 2013 and claims the benefit of JP 2012-057078 filed Mar. 14, 2012.

TECHNICAL FIELD

The present invention relates to a method for producing a sulfur amino acid-comprising composition from a plant belonging to the genus *Allium* and a sulfur amino acid-comprising composition obtained by the method.

BACKGROUND ART

Plants belonging to the genus *Allium* such as Welsh onions, common onions and garlics have long been consumed as foods having a tonic effect. Recently, it has also been known that an L-cysteine sulfoxide derivative, which is a sulfur amino acid contained in plants belonging to the genus *Allium*, has the enhancing action on the production of the male hormone (androgen), testosterone (Patent Literature 1).

However, it is difficult to ingest sulfur amino acids continuously in an amount enough to expect physiological actions only by eating plants belonging to the genus *Allium*. Also, because plants belonging to the genus *Allium* contain not only sulfur amino acids, but also various other components, eating plants belonging to the genus *Allium* themselves is not efficient as a means for ingesting sulfur amino acids. Therefore, there is a demand for the development of a method for concentrating the sulfur amino acid contained in plants belonging to the genus *Allium* and a composition comprising a high content of sulfur amino acid derived from plants belonging to the genus *Allium*.

The aforementioned Patent Literature 1 describes a method for producing a processed product of a plant belonging to the genus *Allium* comprising a high content of an L-cysteine sulfoxide derivative, comprising deactivating C-S lyase, which degrades sulfur amino acids contained in a plant belonging to the genus *Allium*, by subjecting an uncut plant to a heat treatment for 5 to 120 minutes under the conditions of a pressure of 1 to 5 atm and a temperature of 40 to 150° C. Also, the Patent Literature 1 describes that an extract containing an L-cysteine sulfoxide derivative from the aforementioned processed product of a plant belonging to the genus *Allium* is obtained by means of alcohol extraction and concentration under reduced pressure. Also, Patent Literature 2 describes a method for producing a high concentration of S-alkenyl cysteine sulfoxide by treating the edible part of a plant belonging to the family Liliaceae with mannanase, cellulase and pectinase, all of which are plant cell wall-degrading enzymes, and then subjecting the resulting product to an ion exchange resin treatment.

However, all of the products obtained by the aforementioned methods have not been fully satisfactory in terms of the sulfur amino acid content.

CITATION LIST

Patent Literature

[Patent Literature 1] JP-B-4172488
[Patent Literature 2] JP-A-2007-84500

SUMMARY OF INVENTION

Technical Problem

An object of the present invention is to provide a method for efficiently recovering the sulfur amino acid contained in a plant belonging to the genus *Allium*. Another object of the present invention is to provide a composition stably comprising a high concentration of sulfur amino acid derived from a plant belonging to the genus *Allium*.

Solution to Problem

Research conducted by the present inventors revealed a problem associated with the extract containing the L-cysteine sulfoxide derivative described in Patent Literature 1, which is inferior in storage stability due to the deactivation of the L-cysteine sulfoxide derivative by contaminating impurities. In view of the above, the present inventors conducted intensive studies to develop a composition capable of stably comprising sulfur amino acids. As a result, they found that a composition stably comprising a high content of sulfur amino acid can be obtained by heating a plant belonging to the genus *Allium* and treating the heated plant with a γ-glutamyl bond cleaving enzyme, and then subjecting the resulting treated product to ion exchange chromatography, thereby completing the present invention.

That is, the present invention provides a method for producing a sulfur amino acid-comprising composition comprising:
heating a plant belonging to the genus *Allium*;
treating the plant belonging to the genus *Allium* thus heated with a γ-glutamyl bond cleaving enzyme; and
subjecting the resulting enzyme-treated product to ion exchange chromatography.

Advantageous Effects of Invention

According to the method for producing a sulfur amino acid-comprising composition of the present invention, the sulfur amino acid contained in a plant belonging to the genus *Allium* can be efficiently recovered. Also, the composition produced by the production method of the present invention stably comprises a high concentration of sulfur amino acid.

DESCRIPTION OF EMBODIMENTS

The method for producing a sulfur amino acid-comprising composition of the present invention comprises the steps of (1) heating a plant belonging to the genus *Allium*, (2) treating the plant belonging to the genus *Allium* thus heated with a γ-glutamyl bond cleaving enzyme, and (3) subjecting the resulting enzyme-treated product to ion exchange chromatography. Each step in the method of the present invention is preferably carried out under the acidic pH conditions, to prevent deterioration of the sulfur amino acid, unless otherwise required for the purposes of enzymatic reactions and the like. Preferable pH is 5.5 or less, more preferable pH is 4.5 or less.

Examples of the sulfur amino acid comprised in the composition produced by the method of the present invention include S-1-propenyl-L-cysteine sulfoxide, S-propyl-L-cysteine sulfoxide, S-methyl-L-cysteine sulfoxide, S-allyl-L-cysteine sulfoxide and the like. It is preferable that at least one sulfur amino acid selected from the group consisting of the above species of sulfur amino acid be comprised in the composition produced by the method of the present invention.

The plant belonging to the genus *Allium* to be subjected to the method of the present invention is not particularly limited as long as it is a plant belonging to the genus *Allium* and comprising the sulfur amino acid of interest. Examples of the plant include common onions (tamanegi), Welsh onions (negi), spring onions (wakegi), chives (asatsuki), garlic chives (nira), garlics (ninniku), victory onions (gyoja ninniku), Japanese scallions (rakkyo), and leeks (riki) and the like. Among them, common onions, Welsh onions, garlics and Japanese scallions are preferable because they are inexpensive and comprise a large amount of sulfur amino acid. In the method of the present invention, the edible parts of these plants belonging to the genus *Allium* are preferably used. For example, the bulbs of common onions, garlics and Japanese scallions, the leaves of spring onions, baby scallions and garlic chives, and the leaves and pseudostems of Welsh onions are preferably used. Also, because the cortex of the aforementioned plants belonging to the genus *Allium* does not contain a sulfur amino acid, it is preferably removed before subjecting the plants to the method of the present invention.

In the step (1) of the method of the present invention, a plant belonging to the genus *Allium* is heated. C-S lyase, which is a sulfur amino acid-degrading enzyme, contained in the plant belonging to the genus *Allium* is deactivated by this heating operation. By deactivating C-S lyase in this step, enzymatic degradation of the sulfur amino acid is inhibited in the subsequent steps, preventing a reduction in the yield of the product of interest. The conditions of the aforementioned heating are not particularly limited as long as the conditions are such that C-S lyase is deactivated without deteriorating the sulfur amino acid of interest. For example, heating for 5 to 120 minutes at a pressure of 1 to 5 atm and a temperature of 40 to 150° C. is preferable, and heating for 15 to 40 minutes at a pressure of 1 to 2 atm and a temperature of 80 to 120° C. is more preferable.

The aforementioned heating is preferably performed on a plant belonging to the genus *Allium* that is not fragmented. When the inside of a plant belonging to the genus *Allium* is exposed to air by cutting, mincing, perforating and so on, the sulfur amino acid contained therein is degraded, resulting in a reduced content of sulfur amino acid. Accordingly, a plant belonging to the genus *Allium* that is "not fragmented" to be subjected to heating in the present step can be a plant belonging to the genus *Allium* which may be subjected to a process such as cutting, chopping, mincing, perforating and scratching only to such a degree that the degradation of internal sulfur amino acid caused by these processes is very small. For example, in the present invention, the phrase "not fragmented" can be a concept which permits cutting the whole plant belonging to the genus *Allium* in half, quarters, eight equal pieces or 16 equal pieces, although the number of pieces varies depending on the part and size of the plant belonging to the genus *Allium* used. Also, for example, in the present invention, the yield of sulfur amino acid obtained by the method of the present invention from a plant belonging to the genus *Allium* that is "not fragmented" can be 80% or more, preferably 90% or more compared to the yield from an intact plant belonging to the genus *Allium*.

At least some of the sulfur amino acid of interest in the aforementioned plant belonging to the genus *Allium* exists as a precursor bound to glutamic acid. In this precursor, a sulfur amino acid is bound to the γ carboxylic acid group of the glutamic acid via amide bond. Since this precursor can be converted to a sulfur amino acid by cleaving the bond between the γ carboxylic acid group and the sulfur amino acid, the yield of the product of interest can be further increased. The step (2) of the method of the present invention can be a step of releasing the sulfur amino acid of interest by cleaving the γ-glutamyl group by enzymatic reactions from the aforementioned precursor in the plant belonging to the genus *Allium*.

Accordingly, in the step (2) of the method of the present invention, the plant belonging to the genus *Allium* heated in the aforementioned step (1) is treated with a γ-glutamyl bond cleaving enzyme. The γ-glutamyl bond cleaving enzyme used in this step may be an enzyme having an action of cleaving a γ-glutamyl group from a peptide or an amino acid, and examples thereof include γ-glutaminase, γ-glutamyl transferase, γ-glutamyl transpeptidase, γ-glutamyl peptidase and the like. These enzymes may be extracted from animals, plants, microorganisms and the like, or may be commercially available products. Examples of the commercially available product include Glutaminase SD-C100S provided by Amano Enzyme, Inc.

In order to allow the aforementioned enzymatic reactions to fully proceed, it is preferable to fragment the plant belonging to the genus *Allium* heated in the aforementioned step (1) before the enzymatic treatment. A means of fragmentation is not particularly limited, and it encompasses a process such as shredding, mincing, crushing, grinding and the like. These processes can be performed by a known means such as a blender, a mixer, a cutter and a mill. Further, since the fragmented plant belonging to the genus *Allium* is normally too viscous to be directly subjected to an enzymatic treatment, it is preferably diluted approximately 2 to 20-fold with an aqueous solution. Examples of the aqueous solution include water, acidic water, alkaline water and the like. These aqueous solutions are preferably those which are adjusted to have the optimal pH for the γ-glutamyl bond cleaving enzyme to be used later or a pH near the above optimal pH.

The conditions of the γ-glutamyl bond cleaving enzyme treatment can be appropriately set according to the optimal conditions for the enzyme, or the kind of the plant belonging to the genus *Allium* used, the part used, the state of fragmentation, and the like. In general, the amount of enzyme added is, relative to the total amount of the plant belonging to the genus *Allium*, from 0.001 to 1% by mass, preferably from 0.01 to 0.1% by mass. As to the reaction condition, reactions can be carried out approximately for 1 to 24 hours at a temperature of 15 to 65° C., preferably approximately for 2 to 6 hours at 35 to 60° C., at the optimal pH for the enzyme. After completion of the aforementioned enzymatic treatment, it is preferable to deactivate the γ-glutamyl bond cleaving enzyme by heating, adjusting pH, and the like. The reaction product obtained by the aforementioned enzymatic treatment may be subjected to filtration, centrifugation, compression and the like, as needed, to separate a solution containing the sulfur amino acid. Further, the solution thus obtained may also be concentrated.

In the step (3) of the method of the present invention, the reaction product obtained by the enzymatic treatment of the aforementioned step (2) is subjected to ion exchange chromatography. The ion exchange resin for the above ion exchange chromatography may be a cation exchange resin, preferably a strongly acidic cation-exchange resin, more preferably a sulfonic acid-type strongly acidic cation-exchange resin. As the ion exchange resin, a commercially available product can be used, and for example, DIAION (Registered Trademark) UBK-550, DIAION (Registered Trademark) SK1B (the products of Mitsubishi Chemical Corporation), AMBERLITE (Registered Trademark) IR120B, AMBERLITE (Registered Trademark) 200C, DOEWX (Registered Trademark) MSC-1 (The Dow Chemical Company), DUOLITE C26 (Rohm and Haas Company), LEWATIT (Registered Trademark) SP-112 (LANXESS Distribution GmbH) and the like can be favorably used.

Ion exchange chromatography may be performed in accordance with the routine procedure. The enzyme-treated product obtained by the aforementioned step (2) is diluted with distilled water, a buffer and the like, as needed, to provide a sample solution. Preferably, the sample solution is adjusted to have a pH of 1 to 5 before it is passed through an ion exchange resin. This sample solution is passed through the ion exchange resin to allow the sulfur amino acid in the sample solution to be adsorbed to the column. Subsequently, the ion exchange resin is washed with a wash solution such as distilled water, followed by elution of the sulfur amino acid adsorbed to the column with an alkaline eluting solution. Either a strong alkali solution or a weak alkali solution can be used as the eluting solution, and a solution having a pH of 8 to 14 is preferable. An eluate containing the aforementioned sulfur amino acid may be directly used; however, it is preferably concentrated, or further desalinated through a known method, to increase the purity of sulfur amino acid. Further, as needed, a treatment such as desiccation, freeze-drying, solidification, liquefaction, granulation or powderization may also be carried out.

A sulfur amino acid-comprising composition can be produced by the procedure described above. The sulfur amino acid-comprising composition obtained by the method of the present invention stably comprises a high concentration of sulfur amino acid, and thus, is suitable for long-term storage and industrial application.

EXAMPLES

Next, the present invention will be further described in detail with reference to Examples; however, the present invention is not limited to the following Examples.

Example 1

Harvested common onions (Kita momiji 2000) (5000 g) were washed and peeled, and the resulting uncut whole onions were subjected to a heat treatment in a hot water bath of 95° C. for 20 minutes.

The heat-treated common onions were minced by using a mixer (the product of The John Oster Manufacturing Company) and water was added in an amount of 1 mL per g of onion, in which the common onions were dispersed. To the dispersion thus obtained, glutaminase (Glutaminase SD-C100S; the product of Amano Enzyme, Inc.) was added in an amount of 0.025% by mass relative to the total amount of common onions in the dispersion, and reactions were allowed to proceed for two hours at 60° C. After completion of the reaction, the resulting solution was heated at 90° C. for 15 minutes to deactivate the enzyme. The resulting reaction solution was centrifuged at 6,000 rpm for 30 minutes, subjected to suction filtration, and subsequently, freeze-dried, whereby approximately 500 g of a crude common onion extract containing approximately 3% by mass of sulfur amino acid was obtained.

To the aforementioned crude common onion extract, distilled water was added to obtain a 30% (w/v) aqueous solution. Then, 1000 mL of this aqueous solution, which was used as a sample solution, was passed through 500 mL of strongly acidic cation-exchange resin (DIAION SK1B, the product of Mitsubishi Chemical Corporation) regenerated by hydrochloric acid. Subsequently, the sample solution remaining in the column was washed out with 3000 mL of distilled water. Subsequently, 1000 mL of a 5% sodium hydroxide solution (pH=14) was passed through the column to elute the sulfur amino acid adsorbed to the ion exchange resin. Further, 2000 mL of distilled water was added to elute the solution remaining in the column. The eluate eluted with a sodium hydroxide solution and the eluate eluted with distilled water were combined and concentrated on an evaporator (the product of Tokyo Rikakikai Co., Ltd.), followed by desalination, to give a solution containing the sulfur amino acid. The solution thus obtained was freeze-dried to obtain approximately 40 g of a composition containing approximately 28% by mass of sulfur amino acid. The yield of sulfur amino acid obtained by the method of the present Example was approximately 75% relative to the crude common onion extract.

Example 2

Harvested common onions (Kita momiji 2000) (approximately 1500 kg) were washed and peeled, and the resulting uncut whole onions were subjected to a heat treatment in a hot water bath of 95° C. for 20 minutes.

The heat-treated common onions were minced by using a chopper, to which 1000 kg of water was added. Glutaminase (Glutaminase SD-C100S; the product of Amano Enzyme, Inc.) was added thereto in an amount of 0.025% by mass relative to the total amount of common onions in the solution, and reactions were allowed to proceed for two hours at 40 to 60° C. After completion of the reaction, the solution was subjected to solid-liquid separation by using a screw press, and subsequently, concentrated by using a plate-type flush concentrating machine. Further, the resulting solution was subjected to a heat treatment of 90° C. for 30 minutes for enzyme deactivation and sterilization, whereby 200 kg of a crude common onion extract having a Brix of 50 was obtained. The amount of sulfur amino acid in the solution was approximately 1.5% by mass.

The aforementioned 200 kg of crude common onion extract was diluted 2-fold with distilled water. The total volume of the resulting diluted solution, which was used as a sample solution, was passed through 150 L of strongly acidic cation-exchange resin (DIAION SK1B, the product of Mitsubishi Chemical Corporation) regenerated by hydrochloric acid. Subsequently, the sample solution remaining in the column was washed out by passing through 1000 L of water. Subsequently, 500 L of a 5% sodium hydroxide solution (pH=14) was passed through the column to elute the sulfur amino acid adsorbed to the ion exchange resin. Further, 1000 L of distilled water was added to elute the solution remaining in the column. The eluate eluted with a sodium hydroxide solution and the eluate eluted with distilled water were combined, neutralized with hydrochloric acid, and then concentrated by a centrifugal thin film concentrating machine, followed by desalination, to give a solution containing the sulfur amino acid. The solution thus obtained was spray-dried to obtain approximately 7.5 kg of a composition containing approximately 28% by mass of sulfur amino acid. The yield of sulfur amino acid obtained by the method of the present Example was approximately 70% relative to the crude common onion extract.

Comparative Example 1

Harvested common onions (Kita momiji 2000) (approximately 5000 g) were subjected to a heat treatment in accordance with a similar procedure to that of Example 1, and then minced by using a mixer (the product of The John Oster Manufacturing Company). To the minced common onions, water was added in an amount of 1 mL per g of onion, in which the minced common onions were dispersed. The dispersion thus obtained was centrifuged at 6,000 rpm for 30 minutes, subjected to suction filtration, and subsequently, freeze-dried, whereby approximately 500 g of a crude common onion extract containing approximately 2.5% by mass of sulfur amino acid was obtained. To this crude common onion extract, distilled water was added to obtain a 30% (w/v) aqueous solution. Then, 1000 mL of this aqueous solution, which was used as a sample solution, was subjected to a strongly acidic cation-exchange resin treatment in accordance with a similar procedure to that of Example 1. The resulting eluate was concentrated on an evaporator (the product of Tokyo Rikakikai Co., Ltd.), followed by desalination, to give a solution containing the sulfur amino acid. The solution thus obtained was freeze-dried to obtain approximately 22 g of a composition containing approximately 28% mass of sulfur amino acid. The yield of sulfur amino acid obtained by the method of the present Comparative Example was approximately 50% relative to the crude common onion extract.

Comparative Example 2

Harvested common onions (Kita momiji 2000) (approximately 5000 g) were subjected to a heat treatment in accordance with a similar procedure to that of Example 1, and then minced by using a mixer (the product of The John Oster Manufacturing Company). To the minced common onions, water was added in an amount of 1 mL per g of onion, in which the minced common onions were dispersed. To the resulting dispersion, mannanase (Mannanase BGM "Amano" 10, the product of Amano Enzyme, Inc.), pectinase (Pectinase HL, the product of Yakult Pharmaceutical Industry Co., Ltd.) and cellulase (Cellulase A "Amano" 3, the product of Amano Enzyme, Inc.) were each added in an amount of 0.025% by mass relative to the total amount of common onions in the dispersion. The resulting dispersion was left still at 50° C. for 16 hours, and then stirred at 50° C. for two hours. After completion of the reaction, the resulting solution was heated at 90° C. for 15 minutes to deactivate enzymes. The resulting reaction solution was centrifuged at 6,000 rpm for 30 minutes, subjected to suction filtration, and subsequently, freeze dried, whereby approximately 500 g of a crude common onion extract containing approximately 1% by mass of sulfur amino acid was obtained. To this crude common onion extract, distilled water was added to obtain a 30% (w/v) aqueous solution. Then, 1000 mL of this aqueous solution, which was used as a sample solution, was subjected to a strongly acidic cation-exchange resin treatment in accordance with a similar procedure to that of Example 1. The resulting eluate was concentrated on an evaporator (the product of Tokyo Rikakikai Co., Ltd.), followed by desalination, to give a solution containing sulfur amino acid. The solution thus obtained was freeze-dried to obtain approximately 8 g of a composition containing approximately 25% by mass of sulfur amino acid. The yield of the method of the present Comparative Example was presumed to be reduced due to the degradation of the sulfur amino acid of interest by prolonged heating during the enzymatic treatment. The yield of sulfur amino acid obtained by this method was approximately 40% relative to the crude common onion extract.

Comparative Example 3

In accordance with a similar procedure to that of Example 1, 100 g of common onions were heated and then treated with glutaminase to obtain 6 g of a crude common onion extract containing approximately 3% by mass of sulfur amino acid. Then, 2 g of this extract was dissolved in 10 mL of distilled water, to which nine times the volume of ethanol was further added, followed by thorough stirring. The resulting solution was centrifuged at 6000 rpm for 15 minutes to collect 0.1 g of precipitates. The amount of sulfur amino acid in the precipitates was approximately 5% by mass, and the yield of sulfur amino acid by ethanol treatment was approximately 8% relative to the crude common onion extract.

Test Example 1

Powders were prepared by freeze-drying the sulfur amino acid-comprising compositions obtained in Example 1 and Comparative Examples 1 to 3 with excipients (TK16, the product of Matsutani Chemical Industry Co., Ltd.). Further, as a control, the aforementioned excipient was added to the common onions which had been subjected only to a heat treatment in accordance with a similar procedure to that of Example 1, and the resulting mixture was freeze-dried to prepare a powder. Each of the above powders was packed and stored at 40° C. for three months. The content of sulfur amino acid (% by mass) in the composition was measured with time to obtain the ratio with respect to the content at the beginning of storage (residual ratio). For the measurement, S-propyl-L-cysteine sulfoxide (PCSO), which is the major sulfur amino acid contained in common onions, was targeted. The results are shown in Table 1.

TABLE 1

| Composition | PCSO content (% by mass) [values in parentheses indicate residual ratio (%)] | | | |
|---|---|---|---|---|
| | At the beginning | 1M | 2M | 3M |
| Control | 0.3 (100) | 0.2 (67) | 0.2 (67) | 0.1 (33) |
| Example 1 | 5.6 (100) | 5.3 (95) | 4.7 (84) | 4.2 (75) |
| Comparative Example 1 | 4.5 (100) | 3.7 (82) | 3.2 (70) | 2.8 (63) |
| Comparative Example 2 | 1.9 (100) | 1.5 (79) | 1.3 (67) | 1.0 (54) |
| Comparative Example3 | 1.5 (100) | 1.1 (74) | 0.9 (60) | 0.5 (34) |

The invention claimed is:

1. A method for producing a sulfur amino acid-comprising composition, wherein the sulfur amino acid is at least one selected from the group consisting of S-1-propenyl-L-cysteine sulfoxide, S-propyl-L-cysteine sulfoxide, S-methyl-L-cysteine sulfoxide and S-allyl-L-cysteine sulfoxide comprising:
   heating a plant belonging to the genus *Allium*,
   fragmenting the heated plant,
   directly treating the fragmented plant with a γ-glutamyl bond cleaving enzyme to produce an enzyme-treated product, and
   subjecting the enzyme-treated product to ion exchange chromatography to obtain a composition comprising at least one selected from the group consisting of S-1-propenyl-L-cysteine sulfoxide, S-propyl-L-cysteine sulfoxide, S-methyl-L-cysteine sulfoxide and S-allyl-L-cysteine sulfoxide.

2. The method according to claim 1, wherein the γ-glutamyl bond cleaving enzyme is γ-glutaminase, γ-glutamyl transferase, γ-glutamyl transpeptidase or γ-glutamyl peptidase.

3. The method according to claim 1, wherein a strongly acidic cation-exchange resin is used in the ion exchange chromatography.

4. The method according to claim 2, wherein a strongly acidic cation-exchange resin is used in the ion exchange chromatography.

5. The method according to claim 1, wherein the plant belonging to the genus *Allium* is one or more selected from common onions, Welsh onions, spring onions, chives, garlic chives, garlics, victory onions, Japanese scallions, and leeks, and the plant is not fragmented prior to heating.

6. The method according to claim 1, wherein the pH of the plant after heating and before ion-exchange chromatography is adjusted to 1 to 5.

7. The method according to claim 1, wherein the heating the plant comprises heating for 5 to 120 minutes at a pressure of 1 to 5 atm and a temperature of 40 to 150° C.

8. The method according to claim 1, wherein the heating the plant comprises heating for 15 to 40 minutes at a pressure of 1 to 2 atm and a temperature of 80 to 120° C.

9. The method according to claim 1, further comprising deactivating the γ-glutamyl bond cleaving enzyme after the treating and before subjecting to ion-exchange chromatography.

* * * * *